United States Patent [19]

Campbell et al.

[11] Patent Number: 5,693,314
[45] Date of Patent: Dec. 2, 1997

[54] TWO COMPONENT DENTIFRICE FOR THE TREATMENT OF DENTINAL HYPERSENSITIVITY

[75] Inventors: Shannon K. Campbell, Piscataway; Edward Albert Tavss, Kendall Park; Steven W. Fisher, Middlesex; Marilou Joziak, South River; Richard F. Theiler, Bridgewater; Michael Prencipe, Princeton, all of N.J.

[73] Assignee: Colgate Palmolive Company, New York, N.Y.

[21] Appl. No.: 594,605

[22] Filed: Feb. 2, 1996

Related U.S. Application Data

[62] Division of Ser. No. 287,371, Aug. 8, 1994.
[51] Int. Cl.⁶ .................... A61K 7/16; A61K 7/18
[52] U.S. Cl. .................... 424/49; 424/52
[58] Field of Search .................... 424/49–58

[56] References Cited

U.S. PATENT DOCUMENTS

| | | | |
|---|---|---|---|
| 4,933,171 | 6/1990 | Bristow et al. | 424/57 |
| 5,240,697 | 8/1993 | Norfleet et al. | 424/52 |
| 5,352,439 | 10/1994 | Norfleet et al. | 424/52 |
| 5,374,417 | 12/1994 | Norfleet et al. | 424/49 |
| 5,449,509 | 9/1995 | Jackson et al. | 424/49 |
| 5,486,350 | 1/1996 | Norfleet et al. | 424/49 |
| 5,503,823 | 4/1996 | Norfleet et al. | 424/52 |
| 5,505,933 | 4/1996 | Norfleet et al. | 424/52 |
| 5,565,190 | 10/1996 | Santalucia et al. | 424/53 |
| 5,599,525 | 2/1997 | Hsu et al. | 424/49 |
| 5,614,174 | 3/1997 | Hsu et al. | 424/49 |

*Primary Examiner*—Shep K. Rose
*Attorney, Agent, or Firm*—Paul Shapiro

[57] ABSTRACT

A two component desensitizing dentifrice composition is disclosed which comprises a first dentifrice component containing a desensitizing potassium salt such as potassium nitrate and a second dentifrice component containing a second desensitizing agent other than a potassium salt the such as $SnF_2$, the second desensitizing agent being incompatible with the potassium salt, the first and second dentifrice components being maintained separate from the other until dispensed for application to teeth requiring relief from dentine hypersensitivity.

13 Claims, 2 Drawing Sheets

TWO COMPONENT DENTIFRICE FOR THE TREATMENT OF DENTINAL HYPERSENSITIVITY

This is a division, of application Ser. No. 08/287,371 filed Aug. 8, 1994.

BACKGROUND OF THE INVENTION

1. Field of the Invention

The present invention relates to a desensitizing dentifrice composition which eliminates or reduces the discomfort and pain associated with dentinal hypersensitivity and more particularly to a two-component desensitizing dental composition.

2. The Prior Art

Dentinal hypersensitivity is defined as acute, localized tooth pain in response to physical stimulation of the dentine surface as by thermal (hot or cold) osmotic, tactile combination of thermal, osmotic and tactile stimulation of the exposed dentin.

Exposure of the dentine, which is generally due to recession of the gums, or loss of enamel, frequently leads to hypersensitivity. The art has determined that dentine tubules open to the surface have a high correlation with dentine hypersensitivity, Absi, J. Clin. Periodontal. 14,280–4 (1987). Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure and ionic gradients. Tin salts such as $SnF_2$ have been indicated clinically to be efficacious in the reduction of dentinal hypersensitivity. This latter therapeutic effect is believed to be attributable, to a large degree, to the stannous ion ($Sn^{2+}$) component of the salt. $SnF_2$ is believed to be effective in desensitization by occlusion of exposed dentinal tubules wherein deposits of low solubility complexes of tin are formed on the surface of exposed dental tubules effectively blocking the openings. When hypersensitive teeth are treated with dentifrices containing tin salts such as $SnF_2$, Sn deposits accumulate on the tooth surface with each treatment until complete, or virtually complete covering of the exposed dentine tubules occurs. By blocking the tubules, the external stimuli have a diminished effect, resulting in less pain.

It is also known to the art that potassium salts are effective in the treatment of dentinal hypersensitivity. For example, U.S. Pat. No. 3,863,006 discloses that potassium salts such as potassium nitrate when incorporated in toothpastes desensitize the teeth after tooth brushing for several weeks. It is widely believed by those skilled in the art that an elevation in the extracellular potassium concentration in the vicinity of pulpal nerves underlying sensitive dentin is responsible for the therapeutic desensitizing effect of topically applied oral products which contain potassium nitrate. Due to passive diffusion of potassium into and out of the open dentine tubules repeated application of the active ingredient is necessary to build up the necessary concentration in the vicinity of the pulpal nerves.

European Patent 0278744 discloses that when Triclosan, 2,4,4' trichloro-2'-hydroxy-diphenyl ether, is used in combination with a potassium salt an increased desensitizing effect is produced. Wealer et al in an abstract entitled "Effect of Triclosan on Neuromuscular Transmission in the Rat, JDR (Journal of Dental Research) 1994. (Abstract #703) reports that Triclosan in concentrations as low as 10 ppm has a marked inhibitory effect on neuromuscular transmission indicating that Triclosan has an analgetic effect.

The cojoint use of Triclosan and a potassium salt in the treatment of dentinal hypersensitivity would appear to involve two different mechanisms for the relief of hypersensitivity as does the cojoint use of a tin and potassium salts.

Attempts to include mixtures of agents such as Triclosan and $SnF_2$ and potassium salts such as potassium nitrate in a single dentifrice composition have been found to be of limited effect as a means for delivering efficacious amounts of both ingredients to the teeth. In the case of tin salts such as $SnF_2$, stannic salts and insoluble stannous compounds such as $Sn(OH)_2$, $SnO_2$, and $Sn(SO_4)_2$ are formed in the dentifrice, and the precipitate is ineffective in occluding the dentin surface to provide the desired dental effect. Also, prolonged contact between stannous ion and nitrate ion in a single dentifrice results in a reaction of these ions causing a conversion of $NO_3$ into potentially toxic materials.

When Triclosan and $KNO_3$ are combined for use in a toothpaste vehicle it has been determined that the Triclosan is incompatible with $KNO_3$ causing it to separate from suspension in the vehicle and become unavailable as an active agent.

SUMMARY OF THE INVENTION

The present invention encompasses a dentifrice composition which when applied to the teeth contains a desensitizing combination of a potassium salt and a second incompatible desensitizing agent whereby improved pain relief is attained.

The present invention is based upon the discovery that when a source of a potassium salt and a source of a second desensitizing agent which is normally incompatible with potassium salts, which sources have been maintained separate from each other, are combined for the first time on the surface of the teeth, an improved desensitizing effect is obtained as a result of the combined presence of these ingredients. It has been found that by operating in this manner, the compositions of this invention are far more effective in desensitizing teeth than compositions in which either agent is present alone.

In one embodiment of the invention, a dental desensitizing composition which includes a source of a first desensitizing potassium salt such as potassium nitrate and a source of second desensitizing agent are housed in a container wherein the sources are maintained separate from each other and are not admixed until simultaneous application to the teeth is to be performed. In the case of stannous salts such as $SnF_2$ and potassium salts such as $KNO_3$ it has been discovered that dentifrices containing $SnF_2$ and potassium nitrate when admixed immediately prior to application to the teeth, the ingredients do not appreciably immediately react to form insoluble tin nor is there an appreciable loss of nitrate and the resultant dentifrice mixture will contain $SnF_2$ and $KNO_3$ in unreacted form for a time sufficient, e.g. 1 to 10 minutes, to allow these salts in their unmodified, unreacted efficacious form to be applied to the teeth.

It is believed that the improved pain relief obtained from the use of the combination of Sn and K salts is due in part to the gradual $Sn^{2+}$ accumulation on the dentin surface which traps $K^+$ in the tubules, preventing their escape to the external environment, and thereby enhancing their rate of flow to the pulp where they are active in desensitizing the nerves, thereby relieving sensitivity until the tubules are completely covered with $Sn^{2+}$ deposits. By maintaining Triclosan separate from potassium salts in the dentifrice, the full concentration of Triclosan added to the dentifrice remains available for treatment of teeth.

In the Drawings:

FIG. 1 is a partially centrally sectioned elevational view of a collapsible tube containing a pair of separate compartments each of which contains a different dentifrice component such as a gel or paste used for treating or cleaning teeth which compartments terminate at the neck of the tube, so that the contents thereof may be dispensed simultaneously for common application to a toothbrush and brushing of the teeth.

DESCRIPTION OF THE PREFERRED EMBODIMENTS

Figure 1:
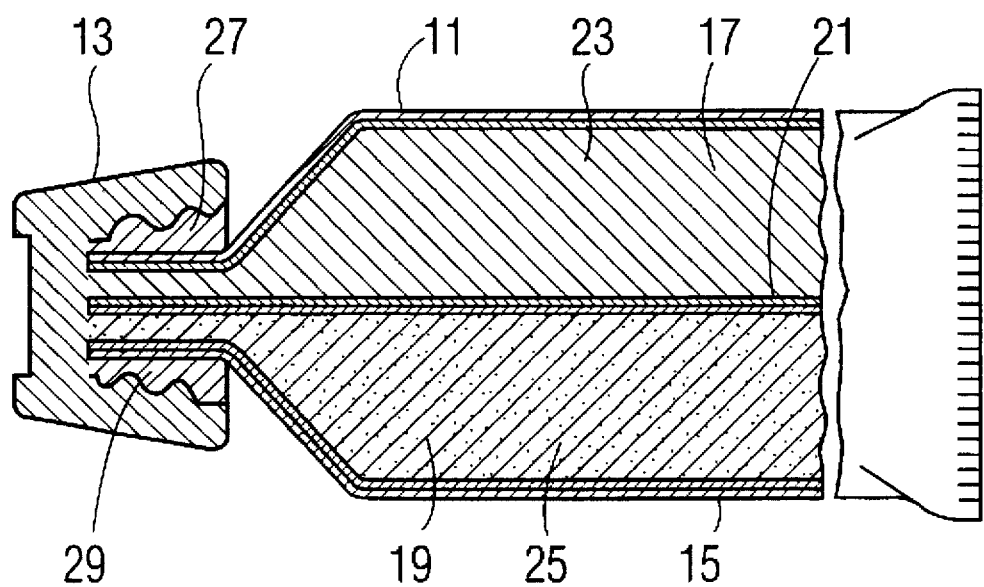

To prepare the potassium salt desensitizing component of the present invention the potassium salt ingredient is generally incorporated in dentifrices which normally include a vehicle which contains water, humectant, surfactant and a polishing agent.

The humectant is generally a mixture of humectants, such as glycerol, sorbitol and polyethylene glycol of molecular weight in the range of 200–1000, but other mixtures of humectants and single humectants may also be employed.

The humectant content is in the range about of 10% to about 80% by weight and preferably about 40 to about 50% by weight. The water content is in the range of about 10 to about 20% by weight.

The source of desensitizing potassium ion is generally a water soluble potassium salt including potassium nitrate, potassium citrate, potassium chloride, potassium bicarbonate and potassium oxalate, potassium nitrate being preferred. The potassium salt is generally incorporated in the compositions of the present invention at a concentration of about 2 to about 15% by weight and preferably about 3 to about 10% by weight.

Inorganic thickeners may be included in the dentifrices in which potassium salts are included as an ingredient thickeners include fumed silicas such as Cabosil available from Cabot Corporation. and thickening silicas including those available from Crosfield Chemicals designated Sorbosil TC-15 or Sylox 15 from W. R. Grace.

Organic thickeners of natural and synthetic gums as colloids may also be incorporated in the dentifrice composition of the present invention in which potassium salts are an ingredient. Examples of such thickeners are carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose. The organic thickener may be incorporated in the compositions of the present invention at a concentration of about 0.1 to about 3% by weight and preferably about 0.5 to about 1% by weight.

Surface active agents may be incorporated in the dentifrices in which a desensitizing potassium salt is included as an ingredient to provide foaming properties. The surface-active material is preferably anionic, nonionic or ampholytic in nature, and most preferably is anionic. Suitable examples of anionic surfactants are higher alkyl sulfates such as potassium or sodium lauryl sulfate which is preferred, higher fatty acid monoglyceride monosulfates, such as the salt of the monosulfated monoglyceride of hydrogenated coconut oil fatty acids, alkyl aryl sulfonates such as sodium dodecyl benzene sulfonate, higher fatty sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the salts of N-lauroyl, N-myristoyl, or N-palmitoyl sarcosine.

Examples of water soluble nonionic surfactants are condensation products of ethylene oxide with various hydrogen-containing compounds that are reactive therewith and have long hydrophobic chains (e.g., aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides and other fatty moieties, and with propylene oxide and polypropylene oxides (e.g., Pluronic® materials).

The surface active agent is generally present in the potassium salt dentifrice compositions of the present invention at a concentration of about 0.5 to about 5.0% by weight.

Abrasives may be incorporated in the potassium salt dentifrice component of the present invention and preferred abrasives are siliceous materials, such as silica, and will normally have a mean particle size up to about 10 microns and a very high surface area e.g. in the range of 150–750 square meters/gram. A preferred silica is a precipitated amorphous hydrated silica, such as Sorbosil AC-35, marketed by Crosfield Chemicals, or Zeodent 115 from Huber Company but other abrasives may also be employed, including sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, sodium bicarbonate, alumina trihydrate, aluminum silicate, zirconium silicate, calcined alumina and bentonite.

The concentration of abrasive in the potassium salt desensitizing dentifrice component composition of the present invention will normally be in the range of 2 to about 40% by weight and preferably 5 to 20% by weight.

Other ingredients which may be incorporated in the potassium salt desensitizing component of the present invention, include pigment, sweetener, flavor and preservative. In white dental cream formulations, the pigment will be titanium dioxide, rutile, and the proportion thereof will normally be in the range of 0.5 to 1% by weight, preferably 0.75 to 1.25% by weight. The sweetener content will normally be that of an artificial or synthetic sweetener and the normal proportion thereof present will be in the range of 0.1 to 1% by weight, preferably 0.3 to 0.5% by weight. The flavor content, which is preferably of a mixed peppermint/menthol flavor, will usually be in the range of 0.5 to 2% by weight, preferably 0.5 to 1.5% by weight. F.D. & C Grade dyes may be used in appropriate amounts to provide desired colors. The contents of other components or adjuvants of the potassium salt containing dentifrice will normally not exceed 10% by weight, often will be less than 5% by weight, and can be as low as 0%.

To prepare the desensitizing potassium salt dentifrice component of the present invention, the humectant and gelling agent are dispersed in a conventional mixer until the mixture becomes a slurry which is smooth in appearance, after which water is added. This mixture may be heated to 100°–110° F. and mixed for 10 to 30 minutes producing a homogeneous gel phase. The potassium salt desensitizing agent is added and mixed for 20 minutes or until completely dissolved. Sweetner and color are added and mixed for 20 minutes. The mixture is transferred to a vacuum mixer. The abrasive is then added and mixed for 10 to 30 minutes at high speed under a vacuum in the range of 5 to 100 millimeter of mercury pressure, preferably 5 to 50 mm Hg, providing a homogenous mixture. The surfactant and flavor are then added to the paste which is followed by mixing another 10 to 20 minutes under vacuum of 5 to 50 mm Hg. The resultant product is a stable desensitizing dentifrice of a texture like that of normal toothpastes or gels having a pH in the range of 5 to 8, preferably 6.5 to 7.5, e.g., 7, and of satisfactory flavor.

In the preparation of the second dentifrice component which contains a stannous salt such as $SnF_2$ due to the chemical instability of such salts in aqueous solutions, the salt is normally applied to the teeth as a nonaqueous gel wherein anhydrous glycerine is a carrier for the tin salt.

The stannous salt gel component of the present invention is generally comprised of about 0.16 to about 2.0% by weight of the stannous salt. In the preparation of gels containing $SnF_2$ the gel contains about 0.30 to about 0.9% by weight $SnF_2$ and preferably 0.35 to 0.85% by weight; about 87 to about 97% by weight anhydrous glycerine and preferably about 90 to about 95% by weight and about 2.0 to about 10.0% by weight of polyethylene glycol having an average molecular weight of 1000 and preferably about 5.0 to about 8.0% by weight.

Although $SnF_2$ is preferred for use in the practice of the invention, stannous salts other than $SnF_2$ may be used in the practice of the present invention. Examples of these stannous salts include stannous chloride, stannous phosphate, stannous citrate and stannous gluconate.

The polyethylene glycol used in the preparation of the $SnF_2$ gel component preferably is a nonionic polymer of ethylene oxide having an average molecular weight of 1000 and the general formula

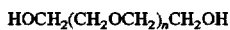

$HOCH_2(CH_2OCH_2)_nCH_2OH$ wherein n represents the average number of oxyethylene groups, such polyethylene glycol being designated hereinafter as polyethylene glycol 1000, the number 1000 representing the average molecular weight.

Also included in the compositions of the present invention is an effective flavoring amount of a flavor compatible and stable with the stannous salt. The flavor ingredient constitutes about 0.05 to about 1% by weight and preferably about 0.1 to about 0.5% by weight of the gel composition. Suitable flavoring constituents are flavoring oils, e.g. oils of spearmint, peppermint, wintergreen, clove, methyl salicylate and menthol.

Thickening agents may optionally be included in the stannous salt gels of the present invention at a concentration of about 0.01 to about 0.8% by weight. Suitable thickening agents include hydroxyethyl cellulose and water soluble salts of cellulose ethers such as sodium carboxymethyl cellulose and sodium carboxymethyl hydroxy ethyl cellulose as well as natural gums.

The stannous salt gel of this invention may be prepared by suspending the salt, flavor and polyethylene glycol 1000 in anhydrous glycerine heated to a temperature of 45° to 140° C. by mixing in any suitable mixer, such as a Lightening mixer for about 30 minutes until a homogenous solution is formed. A substantially rigid non-fluid gel product is obtained upon cooling.

Triclosan when used as the desensitizing agent in the second dentifrice component of the present invention is generally present in the dentifrice component at a concentration of about 0.1 to about 0.5% by weight of the dentifrice component. Triclosan may be incorporated in aqueous based dentifrice vehicles similar to that used for the potassium salt dentifrice. When incorporated in such dentifrice compositions the Triclosan is generally premixed with the flavor and surfactant constituents prior to its addition to the dentifrice vehicle to promote the dispersion of the Triclosan in the dentifrice composition.

Any convenient means for effecting the separation of the potassium salt from the stannous salt or triclosan dentifrice components before use can be utilized. For example, a single container can be compartmentalized so that a $SnF_2$ containing dentifrice component and a potassium salt containing component are housed in separate compartments and are not admixed until applied to the teeth. Alternatively, the $SnF_2$ containing component and the $KNO_3$ containing component can be housed in separate containers from which the respective phases are dispensed for admixture just prior to use.

Thus for example, in the embodiment as shown in FIG. 1, segregated dentifrice compositions are housed in a common container and are separated from one another by a barrier, such as a wall integrally formed with the container which prevents mixing prior to the compositions being dispensed.

In FIG. 1, dispensing tube 11, equipped with cap 13 to close it off on storage and between uses, includes a body 15 and two interior compartments 17 and 19, which may be considered as contacting each other along surfaces 21. As illustrated, the compartments contain first and second dentifrice components 23 and 25 of the two component dentifrice of this invention. The threaded collar 27 on the neck portion 29 of tube 11 helps to rigidify such neck. The dentifrice composition of the present invention will be dispensed simultaneoulsy as two ribbons when the tube is collapsed by hand pressure.

The following examples are further illustrative of the present invention, but it is understood that the invention is not limited thereto. All amounts and proportions referred to herein and the appended claims are by weight.

Example 1

A $SnF_2$ gel useful as a component of the two component dentifrice of the present invention was prepared with the following ingredients:

| SnF$_2$ Gel | |
|---|---|
| Ingredient | Concentration (wt %) |
| Glycerine | 92.700 |
| Polyethylene glycol 1000 | 6.00 |
| SnF$_2$ | 0.8000 |
| Flavor (Creme de menthe) | 0.50 |

The glycerine, flavor and polyethylene glycol 1000 were premixed at 100° C. for 30 minutes to form a homogenous solution. The solution was then mixed with $SnF_2$ for 30 minutes at a speed of 800 revolutions/min with a Lightning mixer. When allowed to cool, a gel product is formed.

A potassium nitrate paste useful as a component of the two component dentifrice of the present invention was prepared with the following ingredients:

| KNO₃ Toothpaste | |
|---|---|
| Ingredient | Weight Percent |
| Sorbitol | 23.30 |
| Glycerin | 17.0 |
| Zeodent 115 | 18.00 |
| Deionized water | 21.00 |
| Sylox 15 | 5.00 |
| Potassium nitrate | 10.00 |
| Polyethylene glycol 600 | 3.00 |
| Sodium Lauryl Sulfate | 1.20 |
| Carboxymethyl Cellulose | 0.60 |
| Sodium saccharin | 0.30 |
| Flavor | 0.60 |
| Total | 100.00 |

The glycerine, sorbitol, polyethylene glycol, carboxymethyl cellulose were dispersed in a conventional mixer until the mixture became a slurry, which was smooth in appearance, water was added and mixed for 10 to 30 minutes producing a homogeneous gel phase in which the potassium nitrate was dispersed. Color and sweetner were added mixed for 20 minutes, and transferred to a vacuum mixer. The siliceous agents were then added and mixed for 10 to 30 minutes at high speed under a vacuum of about 50 mm Hg, providing a homogenous mixture. The sodium lauryl sulfate and flavor were then added to the paste which was followed by mixing another 20 minutes under vacuum of 50 mm Hg. The resultant product was a toothpaste with satisfactory flavor.

The $SnF_2$ Gel and $KNO_3$ Toothpaste prepared above were of extrudable consistency. After 2 days of storage, separate ribbons of the two dentifrices were extruded sequentially onto the bristles of a toothbrush. Five minutes after the ribbons were mixed together, the mixture was analyzed for $SnF_2$. Analysis indicated the presence of 0.4% stannous ion as stannous fluoride indicating that 100% of the original stannous ion was available for effective treatment of dentinal hypersensitivity.

For purposes of comparison, the procedure of Example 1 was repeated except that 0.4% $SnF_2$ was included in the $KNO_3$ Toothpaste. This composition had the following ingredients:

| Comparative Toothpaste | |
|---|---|
| Ingredient | Weight Percent |
| Sorbitol | 35.16 |
| Deionized water | 10.04 |
| Glycerin | 20.30 |
| Zeodent 115 | 18.00 |
| Sylox 15 | 5.00 |
| Potassium nitrate | 5.00 |
| Stannous Fluoride | 0.40 |
| Polyethylene glycol 600 | 3.00 |
| Sodium Lauryl Sulfate | 1.20 |
| Carboxymethyl Cellulose | 0.60 |
| Sodium saccharin | 0.30 |
| Flavor | 0.60 |
| Total | 100.00 |

Two days of storage at ambient room temperature the Comparative Toothpaste was analyzed for stannous ion and was found to contain 0.334% stannous ion as $SnF_2$ indicating only 83.5% of the original stannous ion was present in the toothpaste.

To determine the effect in aging on the Comparative Toothpaste, samples of the toothpaste were placed in collapsible laminate tubes and exposed to heated air at 105° F. for a period of 12 weeks. Analysis of aged toothpaste samples indicated the presence of 0.213% stannous ion indicating that about two thirds of the original stannous ion present in the toothpaste had been lost.

Aging tests were repeated with the $SnF_2$ Gel of Example 1 which had been maintained separate from the potassium nitrate dentifrice and aged at 105° C. for period of 12 weeks. The analysis of the aged $SnF_2$ Gel indicated virtually no loss of stannous ion (0.39% $SnF_2$) indicating that if stannous ion is maintained in an anhydrous vehicle and not mixed with an aqueous dentifrice until the time of use, then virtually the entire amount of the originally added $Sn^{+2}$ salt can be applied to the oral cavity to provide hypersensitive benefits.

Example 2

The two component $SnF_2/KNO_3$ dentifrice composition of the present invention was determined to exhibit improved efficacy against dentinal hypersensitivity.

The efficacy of the two component $SnF_2$ Gel, and $KNO_3$ Toothpaste of Example 1 was demonstrated in accordance with an in vitro procedure found to correlate with clinical efficacy. In this procedure eight hundred micron thick coronal dentine disks were cut from human molars and etched for 2 minute in 6 percent citric acid to remove the smear layer. The coronal side of each disk was then given multiple 60 second in vitro treatments (3 times daily) of the two component dentifrice for 10 days using a soft toothbrush followed by brief rinsing. The two component dentifrice was applied to the disks immediately following their being applied to the brush. Disks were continuously rinsed by fresh, 37° C. phoshate buffer (0.1 mM Ca, 0.06 mM $PO_4$, 0.1M NaCl) between treatments. After treatment, the disks were rinsed well in deionized water and dried. The so treated coronal surfaces were examined by a scanning electron microscope to determine the level of dentine tubule occlusion, the level of occlusion being approximately proportional to the degree of relief from hypersensitivity pain expected from the treatment.

Figure 2:
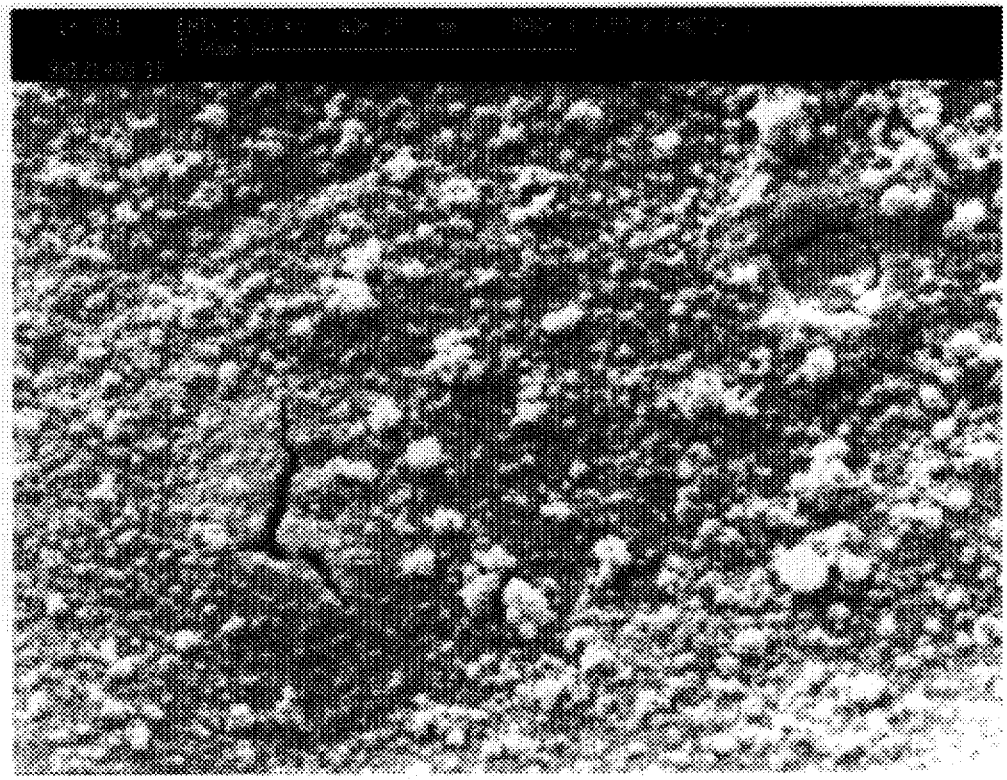
FIG. 2 is a scanning electron photomicrograph (7,500× magnification) of a dentin disk surface treated with a gel containing both tin and potassium salts.
Figure 3:
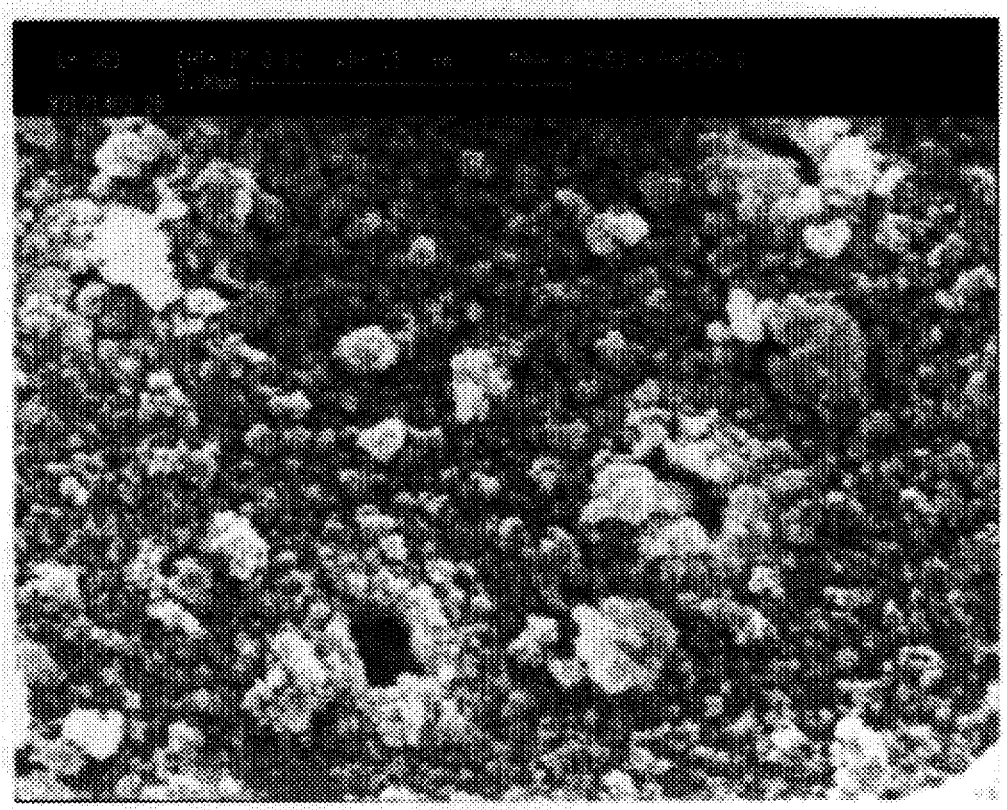
FIG. 3 is a scanning electron photomicrograph (7,500× magnification) of dentin disk surface treated simultaneously with separately extruded tin and potassium salt dentifrices.

For purposes of comparison, the procedure of Example 2 was repeated using the Comparative Toothpaste prepared above containing both $SnF_2$ and $KNO_3$ salt ingredients Photomicrographs taken of the coronal surfaces (FIGS. 2 and 3) show a more complete deposit of material on the dentin disks treated with the separately applied $SnF_2$ Gel and $KNO_3$ Toothpaste of Example 1 (FIG. 3) then with the Comparative Toothpaste (FIG. 2). The granular surface shown on the disks are silica which is labile and offers no long term protection against hypersensitivity.

Elemental analysis of the coronal surface indicated that as compared to the Comparative Toothpaste, substantially more stannous ion is deposited on the dentin disk treated with the two component dentifrice of Example 1. The analysis results are recorded in the Table below.

TABLE

|  | % Sn on Coronal Surface |
| --- | --- |
| Two Component Dentifrice (Ex. 1) | 1.28 |
| Comparative Toothpaste | 0.93 |

What is claimed is:

1. A two component desensitizing dentifrice composition which eliminates or reduces the discomfort and pain associated with dentinal hypersensitivity which comprises a first dentifrice component containing a desensitizing potassium salt and a second dentifrice component containing a second desensitizing agent other than a potassium salt, the second desensitizing agent being incompatible with the potassium salt, the first and second dentifrice components being maintained separate from each other until dispensed for application to teeth requiring relief from dentine hypersensitivity.

2. The composition of claim 1 wherein the potassium salt is potassium nitrate.

3. The composition of claim 1 wherein the second desensitizing agent is Triclosan.

4. The composition of claim 3 wherein the second dentifrice is an anhydrous gel.

5. The composition of claim 1 wherein the second dentifrice component is an aqueous dentifrice.

6. The composition of claim 2, wherein the second dentifrice contains an abrasive.

7. The composition of claim 1 wherin the first dentifrice component is an aqueous dentifrice containing potassium nitrate and the second dentifrice is an aqueous dentifrice containing Triclosan.

8. The composition of claim 1 wherein the potassium salt is potassium nitrate.

9. The composition of claim 1 wherein the second desensitizing agent is Triclosan.

10. The composition of claim 2 wherein the second dentifrice is an anhydrous gel.

11. The composition of claim 1 wherein the second dentifrice component is an aqueous dentifrice.

12. The composition of claim 3 wherein the second dentifrice contains an abrasive.

13. The composition of claim 1 wherin the first dentifrice component is an aqueous dentifrice containing potassium nitrate and the second dentifrice is an aqueous dentifrice containing Triclosan.

* * * * *